United States Patent
Velázquez

(10) Patent No.: US 6,699,226 B2
(45) Date of Patent: Mar. 2, 2004

(54) DEVICES, METHODS, AND KITS FOR COLLECTING SEMEN

(76) Inventor: Víctor E. Velázquez, P.O. Box 8538, Humacao, PR (US) 00792

( * ) Notice: Subject to any disclaimer, the term of this patent is extended or adjusted under 35 U.S.C. 154(b) by 0 days.

(21) Appl. No.: 09/930,639

(22) Filed: Aug. 14, 2001

(65) Prior Publication Data

US 2003/0036737 A1 Feb. 20, 2003

(51) Int. Cl.$^7$ ............................................. A61F 5/44
(52) U.S. Cl. .................... 604/349; 604/540; 604/355; 604/906; 600/35; 128/918
(58) Field of Search ................... 604/540, 317, 604/327, 346, 347, 349, 352, 355, 906; 600/35; 128/844, 918; D24/121, 122

(56) References Cited

U.S. PATENT DOCUMENTS

| | | | | |
|---|---|---|---|---|
| 3,951,141 A | * | 4/1976 | Kopelowicz | 604/351 |
| 4,498,466 A | * | 2/1985 | Pomeranz | 600/39 |
| 4,527,988 A | * | 7/1985 | Lutz et al. | 604/349 |
| 4,726,359 A | * | 2/1988 | Schroeder | 128/844 |
| 4,820,290 A | * | 4/1989 | Yahr | 604/349 |
| 5,102,405 A | * | 4/1992 | Conway et al. | 604/352 |
| 5,244,096 A | * | 9/1993 | Stoner | 206/581 |
| 5,421,350 A | * | 6/1995 | Friedman | 128/844 |
| 5,458,114 A | * | 10/1995 | Herr | 128/842 |
| 5,513,654 A | * | 5/1996 | Delson | 128/844 |
| 5,685,871 A | * | 11/1997 | Lindholm-Ventola | 604/349 |
| 5,927,278 A | * | 7/1999 | Omrani | 128/844 |
| 6,028,115 A | * | 2/2000 | Zaneveld et al. | 514/709 |
| 6,035,854 A | * | 3/2000 | Blake | 128/844 |
| 6,145,507 A | * | 11/2000 | Hardy | 128/844 |
| 6,148,819 A | * | 11/2000 | Winkler | 128/842 |
| 6,250,303 B1 | * | 6/2001 | Delaney | 128/844 |
| 6,298,853 B1 | * | 10/2001 | Blake | 128/844 |
| 6,367,477 B2 | * | 4/2002 | Lee | 128/842 |
| 6,491,035 B2 | * | 12/2002 | Winkler | 128/842 |
| 6,520,922 B2 | * | 2/2003 | Michelle | 600/562 |
| 2002/0165673 A1 | * | 11/2002 | Morgan | 702/19 |

FOREIGN PATENT DOCUMENTS

EP          0 324 557     *  7/1989      ............. A61F/5/43

* cited by examiner

*Primary Examiner*—Weilun Lo
*Assistant Examiner*—Michael Bogart

(57) ABSTRACT

The present invention comprises devices, methods, and kits for collecting semen and other biological fluids. The devices comprise a container that has an opening that fits on a glans of a penis, preferably only the distal portion of the glans, wherein said opening has an adhesive that detachably adheres the device to the penis. The present invention facilitates stimulating the penis to achieve ejaculation, the hygienic collection and secure storage of semen, and transferring the collected semen to other containers.

48 Claims, 5 Drawing Sheets

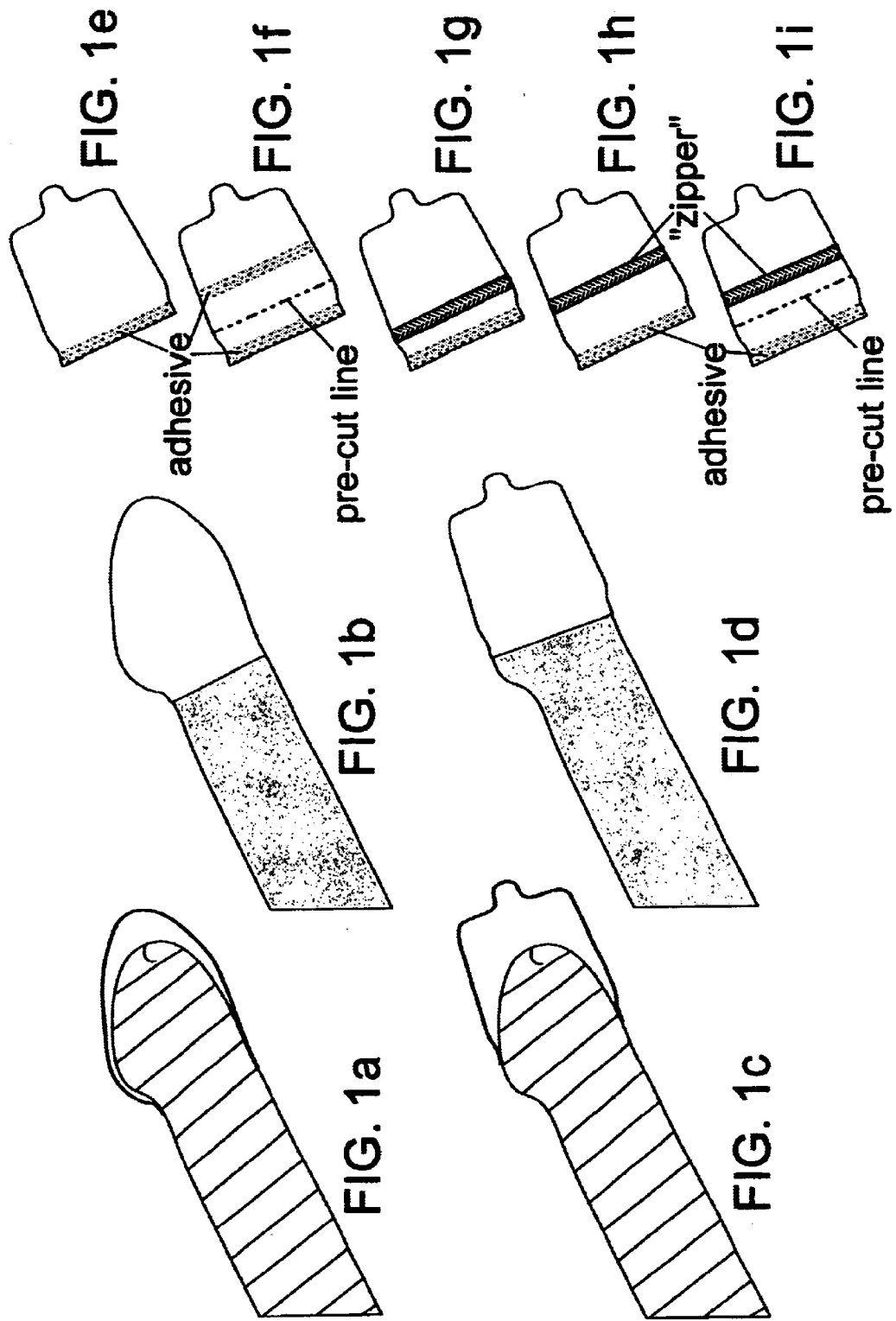

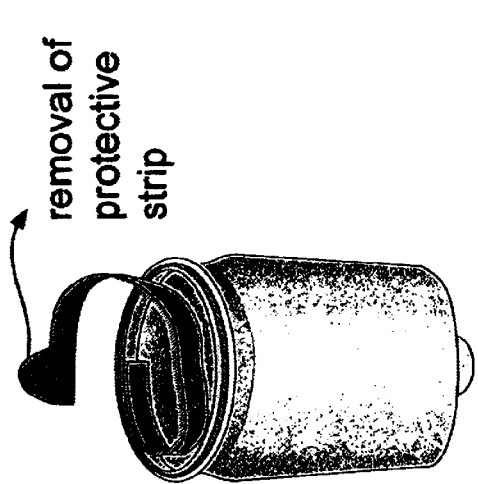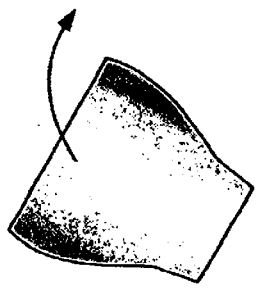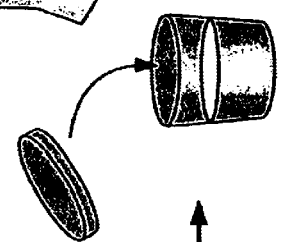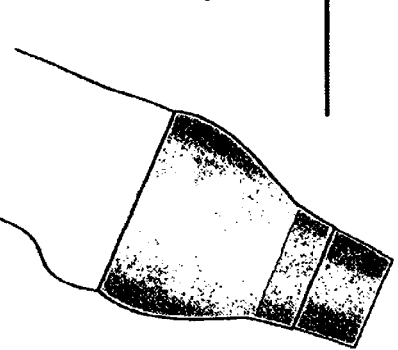

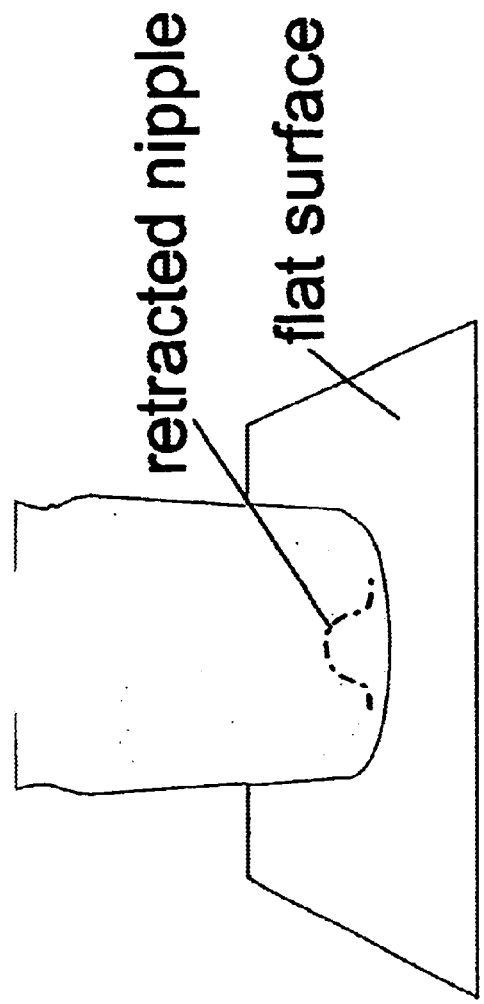
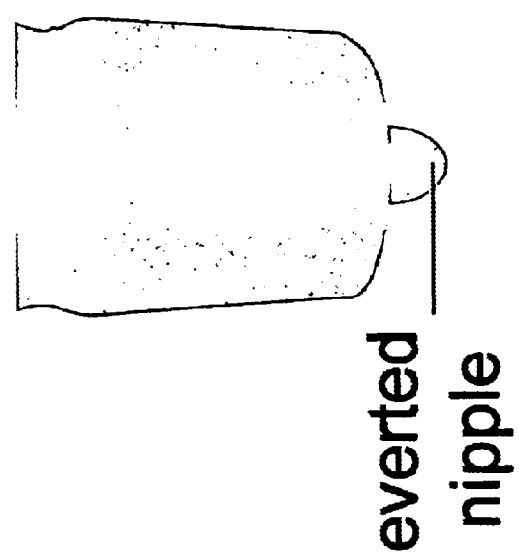
FIG. 4b
FIG. 4a

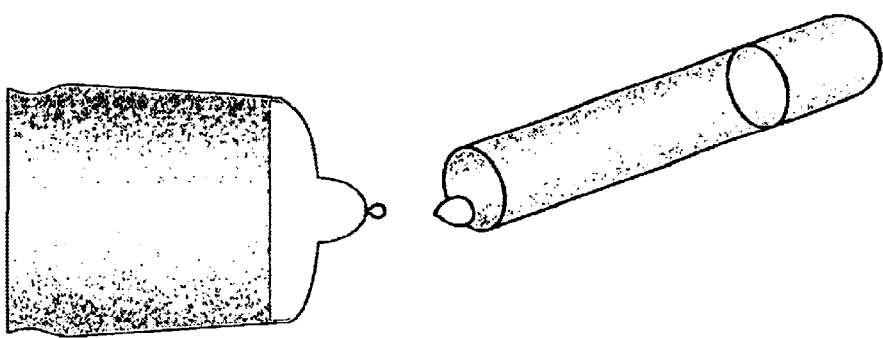
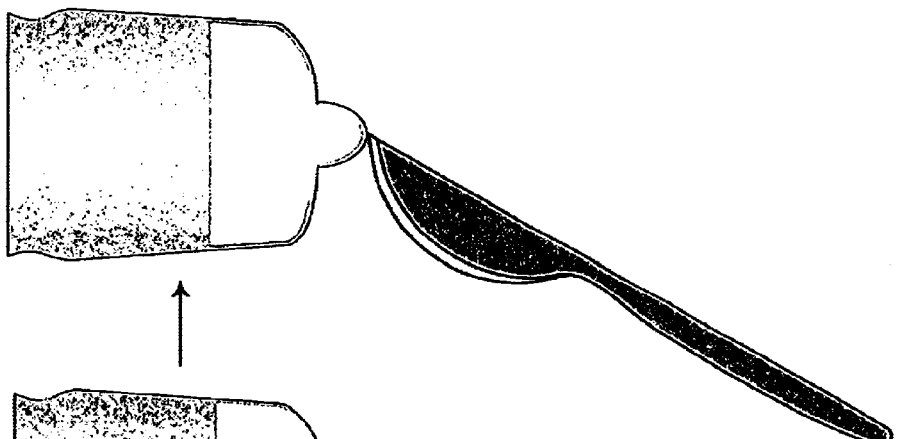
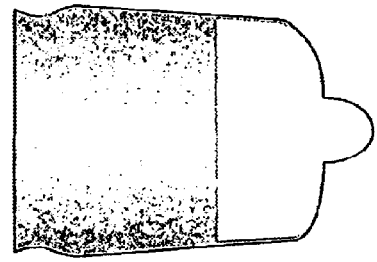

DEVICES, METHODS, AND KITS FOR COLLECTING SEMEN

BACKGROUND OF THE INVENTION

Collecting semen is important for a variety of reasons, most notably for fertility studies, for artificial insemination and for propagating desirable traits in livestock.

Traditionally, semen is collected from human patients by having them ejaculate into a condom or a cup. Both methods are inadequate. Condoms reduce penile sensation and inhibit masturbatory ejaculation. They are also somewhat bulky, and often unhygienic and messy to remove, the condom lubricants may contaminate the semen sample, and it is hard to transfer the semen from a condom to a more manageable container. Cups are not only coldly clinical but also distracting, as they require some concentration, coordination, dexterity and aim to ensure that the semen ends up in the cup.

The most common method of collecting semen in animals is by the use of an artificial vagina. This usually consists of a tube having an interior liner, which leads to a cone that is connected to a test tube for collecting the semen. The prior art is replete with artificial vaginas that can be used, for example as depicted in U.S. Pat. Nos. 2,441,868; 3,421,504; 3,631,853; 3,910,262; 4,059,100; and 4,312,350. Alternatively, semen is collected by placing a cup-like material inside the vagina of a receptive female.

The present invention is intended to overcome the deficiencies of traditional methods. The present invention provides devices and methods for the improved collection of semen, and also devices and methods for processing the semen once it is collected.

BRIEF DESCRIPTION OF THE FIGURES

FIG. 1 depicts several embodiments contemplated in the present invention, particularly illustrating how the device fits over the glans (FIGS. 1a–1d) and alternative placements of adhesive bands and "zippers" (FIGS. 1e–1i).

FIG. 3 is a relief drawing of several embodiments of the present invention, particularly illustrating different possible layers at the adhesive band (FIG. 2e), and that the device may be sealed (FIGS. 2b and 2d).

FIG. 4 illustrates how the flexible protruding region of the device, shaped like a hollow nipple in this embodiment, is retracted into the interior of the device to allow the device to stably sit on a surface.

FIG. 5 illustrates how the protruding region of the device may be cut to facilitate transfer of the collected semen to a second container.

SUMMARY OF THE INVENTION

Figure 2A:
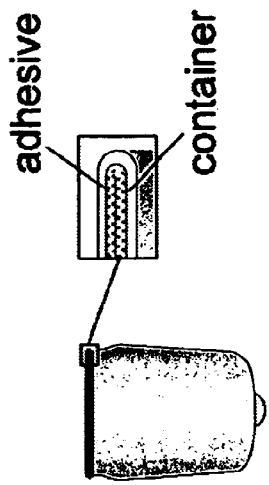
FIG. 2 is a relief drawing of several embodiments of the present invention, particularly illustrating different ways the adhesive may be configured and used to seal the device.

A main embodiment of the present invention is a device for collecting semen, comprising a container that has an opening that fits on a glans of a penis, wherein said opening has an adhesive that detachably adheres the device to the penis. The device preferably further comprises a flexible protruding region that may be retracted to allow the container to stably rest upon on a surface (see FIG. 4). This protruding region may be cut to transfer collected semen to a second container such as a test tube (see FIG. 5).

The container is made of a material that may be impermeable or selectively permeable, and/or opaque or transparent, and/or temperature resistant. This container is optionally sterile, colored or scented.

The adhesive is preferably disposed in a band or rim at the open edge of the container. In some embodiments, the device includes more than one (e.g., at least two, three, or four) adhesive bands, optionally separated by a pre-scored discontinuous line that may be cut or torn. Opposite regions of an adhesive band may be brought into contact with each other to seal the collected semen inside the container.

The device of the present invention may also further comprise a "zipper" for sealing collected semen inside the container. The "zipper" may be zipped to seal the collected semen inside the container.

The device may further comprise a pre-cut discontinuous line between the adhesive region and the "zipper." The pre-cut line may be torn or cut to separate the adhesive band away from remainder of the container with the collected semen.

The device of the present invention may further comprise a medicament, such as: a general antibiotic, an antiviral, an antifungal, an antibacterial, a compound that inhibits the growth of a specific target group of organisms (e.g., an inhibitor of gram negative bacteria), a hormone, a nucleic acid, an antibody, an immune system modulator such as a cytokine, and any combination thereof.

The device of the present invention may also comprise a reactive or indicator material that may be used to detect a property of the collected semen, such as pH, temperature, or presence or concentration of a desired analyte such as sodium, ATP, sperm markers, seminal fluid markers, etc.

The device of the present invention may also further comprise a composition of matter that may be used to alter a property of the collected semen, such as a buffer for controlling the pH of the collected semen, or a salt composition, or a detergent, or a ligand (e.g., antibody, hormone, hormone agonist or antagonist, membrane receptor agonist or antagonist) for any molecule that may be present in semen sample, or any combination thereof.

The device of the present invention may further comprise a region for storing desired information. The desired information may include demographic data of the semen donor (e.g., species, name, age, sex, medical history, vital medical statistics such as past or present medical diseases or known medical susceptibilities, genotypic information, family medical history, sperm count, sperm motility index), and/or the date the semen was collected and/or frozen and/or used; and/or what the semen was used for. The region for storing desired information may simply be an area of the surface of the container that can be handwritten on, for example a printed colored square, or printed lines on a colored background. Alternatively, the region for storing desired information comprises a machine-readable element, such as for example a printed bar code or a microchip. This desired information may be pre-stored in machine-readable form, and it may be in a read-only format. In addition, the region for storing desired information may comprise a machine-writable element into which desired information may be encoded at will in a machine-readable format.

Another main embodiment of the present invention is a method for collecting semen, comprising the steps of:
placing on a glans of a penis a device for collecting semen, wherein said device comprises a container having an opening that fits on a glans of a penis, wherein said opening has an adhesive material that detachably adheres the device to the penis;

inducing the penis to ejaculate;

detaching the device from the penis together with the ejaculated semen; and sealing the collected semen inside the detached device.

The method of the present invention may also comprise adding a medicament to the collected semen, and/or dialyzing the collected semen against a solution having a desired composition, and/or freezing the collected semen.

Another main embodiment of the present invention is a kit, comprising a device for collecting semen, and instructions for using the device to collect semen. The kit may further include a medicament that may be added to the collected semen, and/or a composition of matter that may be used to detect a property of the collected semen, and/or a composition of matter that may be used to alter a property of the collected semen (e.g., pH), and instructions for their use. The kit may further include a device for reading machine-readable information, and a device for entering machine-writable information in the storage area of the device.

DETAILED DESCRIPTION OF THE INVENTION

A. Definitions

The term "animal" as used herein is generally intended to cover, for example, bulls, stallions, boars, rams, and dogs; however, it should be understood that it is not so limited and that the term animal can apply to humans.

The term "medicament" denotes any substance or composition of matter that is used to treat a medical condition. It includes but is not limited to: a general antibiotic, an antiviral, an antifungal, an antibacterial, a bacteriocide, a bacteriostat, a compound that inhibits the growth of a specific target group of organisms (e.g., an inhibitor of gram negative bacteria), a hormone, a nucleic acid, an antibody, an immune system modulator such as a cytokine, and any combination thereof.

B. The Invention

It is one purpose of the present invention to provide devices and methods for the improved collection of semen. It is further a purpose of the present invention to provide devices and methods for readily and efficiently processing the semen once it is collected.

Accordingly, a main embodiment of the present invention comprises a device for collecting semen, comprising a container that has an opening that fits on a glans of a penis (see, e.g., FIGS. 1a–1d), wherein said opening has an adhesive that detachably adheres the device to the penis (see, e.g., FIGS. 1e–1i and FIG. 2). The shape of the container (e.g., FIGS. 1a and 1b, or FIGS. 1c and 1d) is not critical, so long as the opening in the container with the adhesive fits snugly on the penis and there is a space near the tip of the penis for collecting semen. Preferably, the device covers only the glans, leaving the shaft free for enhanced sensation and manipulation (see, e.g., FIGS. 1a–1b). In a most preferred embodiment, the device covers only the distal portion of the glans, leaving the sensitive corona of the glans exposed (see, e.g. FIGS. 1c–1d). Thus, unlike a condom, which covers most of the sensitive surface of the penis, the device of the present invention leaves the bulk of the penile surface exposed. The present invention therefore facilitates stimulating the penis to achieve ejaculation.

The container is generally made of a material that is flexible, elastic, light, friction and tear-resistant, opaque or transparent, and temperature resistant (e.g., different container materials are resistant to temperatures that range sub zero to about 45 degrees Centigrade). The container components should not contaminate the collected semen, nor react with semen components. The container material may be anti-static, and/or biodegradable but stable. The container may, for example, be made of a material selected from a list that includes polyvinyl, latex, polyurethane, polyethylene, polypropylene, polycarbonate, cellulose, and any combination thereof.

The container is preferably impermeable to semen components. However, for any uses that call for changing the composition of the semen, the container may be semi-permeable to allow the passage of small molecules such as water and dissolved elements, or small compounds such as amino acids and simple sugars; or larger molecules such as proteins and hormones. The sperm is collected, the container is sealed (a dialysis clip may be affixed to the container to further prevent leakage) and it is dialyzed against a buffer, for example a saline solution or a phosphate buffer.

The exact shape (see, e.g., FIGS. 1a–1d) and exact dimensions of the container may vary to accommodate the penis of the semen donor. For example, the container may be substantially cylindrical or slightly conical (see, e.g., FIGS. 1c–1i). The diameter at the open edge of the container can measure between about 1 to about 10 cm. (e.g., 1 or 2 or 3 or 4 or 5 or 6 or 7 or 8 cm, or fractional (e.g., millimeter or ten thousands of a meter) increments thereof, such as 3.0 or 3.1 or 3.2 or 3.3 or 3.4 or 3.5 or 3.6 or 3.7 or 3.8 or 3.9 or 4.0 or 4.1 or 4.2 or 4.3 or 4.4 or 4.5 or 4.6 or 4.7 or 4.8 or 4.9 or 5.0 or 5.1 or 5.2 or 5.3 or 5.4 or 5.5 or 5.6 or 5.7 or 5.8 or 5.9, etc.). The container may measure between about 1 cm. to about 30 cm. in length from the open edge to the distal tip of the container, in similar increments as the diameter.

The container may alternatively comprise a cup at the distal end of the device and a second flexible material that is adhered to the cup (see, e.g., FIG. 3c) which attaches the cup to the penis (see, e.g., FIG. 3d). Once the semen is collected, the flexible material is detached and the cup with the collected semen may be capped with a removable cap (see, e.g., FIG. 3e).

The identity of the adhesive is not critical, so long as the adhesive (a) adheres the device to the penis so as to prevent the device from detaching as the semen is collected, (b) does not contaminate the collected semen nor react with semen components, and (c) readily detaches from the penis after semen is collected without causing injury or pain to the penile skin. The general prior art in the field of topical adhesives for attachment to the skin is particularly developed in the field of Band-Aids, plasters and bandages; any of these may be used in the present invention. The following references provide a comprehensive overview of medical and other adhesives: Flanagan, Handbook of Adhesive Bonding (McGraw-Hill Book Co., 1973) ch. 8, pp. 1–17. Landrock, ADHESIVES TECHNOLOGY HANDBOOK (Noyes Publications, 1985); Miyauchi, J. Polymer Sci.: Polymer Chem. Edition 19:1871–1873 (1981); S. C. Temin, in the ENCYCLOPEDIA OF POLYMER SCIENCE AND ENGINEERING, vol. 13 (New York: John Wiley & Sons, 1988), at pp. 345–368, and the HANDBOOK OF PRESSURE-SENSITIVE ADHESIVE TECHNOLOGY, ed. Donates Satas (New York: Van Nostrand Reinhold Co., Inc., 1982). See, e.g., U.S. Pat. Nos. 4,140,115; 4,460,371; 4,593,053; 4,699,146; 5,071,704; 5,418,052; 5,445,627; 5,536,768; 5,559,165; 5,658,270; 6,177,482; 6,191,189 and foreign patent documents CH 643 730, EP 0 184 470, EP 0 611 575 A1, FR 2 734 574, GB 2 115 431, JP 55-092306, JP 62-209008, WO 93/10201, WO 95/16424, WO 96/14822, and WO 96/13238. See also U.S. Pat. Nos. 4,080,348;

4,136,071; 5,039,750; 5,156,911; 5,176,956; 5,274,036; 5,306,504; 5,462,538; 5,653,769; 5,741,510; 5,811,116; 5,840,072; 5,876,855; 5,891,957; 5,916,968; 5,935,596; 5,942,065; 5,948,400; 5,985,300; 6,096,333; 6,096,334; and 6,108,818; and foreign patent documents EP 0333936 and EP 0683187. Since the penile skin might sweat or be exposed to moisture during semen collection, the adhesive should not detach if exposed to moisture. Adhesives having good wet skin adhesion are described in U.S. Pat. No. 5,613,942; 5,785,985; 6,198,016 and 6,197,845. Also, to allow the skin to breathe, the adhesive may be disposed in a discontinuous pattern, as disclosed in U.S. Pat. Nos. 4,595,001 and 5,613,942, as well as EP 353972 and EP 91800 which describe the patterned design of adhesives using a release coated calender roll or screen printing. The adhesives may have a peel force of less than 10 N/dm, preferably from about 3 N/dm to about 6.0 N/dm. The adhesive used in the devices of the present invention may be selected from any adhesive mentioned in the above-cited references, including: cyanoacrylates (e.g., octylcyanoacrylate, butylcyanoacrylates), a styrene-isoprene-styrene copolymer, a cross-linked polyvinylpyrrolidone hydrogel, a poly(n-vinyl lactam), acrylic-based adhesives which contain an unreacted polyol plasticizer, hydrophobic polyoxyalkylene-based adhesives derived from poly(ethylene glycol) prepared in the presence of a plasticizer; silicone-based pressure sensitive adhesives; combinations of acrylic pressure sensitive adhesive and one of an elastomer with a tackifying resin or a thermoplastic elastomer; hydrocolloid adhesives; polyurethane foam, a polyurethane foam/polyurethane film laminate; AD2000 (Medical Design and Manufacturing West 2000, Anaheim, Calif., USA) and any combination thereof.

The adhesive is preferably disposed in a band or rim at the open edge of the container (see, e.g., the yellow bands in FIGS. 1e–1i and FIG. 2). The band may measure between about 0.1 and 1 cm in width. In some embodiments, the device may include more than one (e.g., at least two or three) adhesive bands (see, e.g., FIG. 1f). The adhesive band may be applied directly to the container material (see, e.g., FIG. 2a). Alternatively, for increased comfort a cushion layer (for example, a pharmaceutically acceptable plastic foam) may be inserted between the adhesive band and the container material (see, e.g., FIG. 3a). In certain embodiments, the adhesive may be replaced or supplemented by a band of elastic material, and/or by making the container of an elastic material.

Figure 2B:
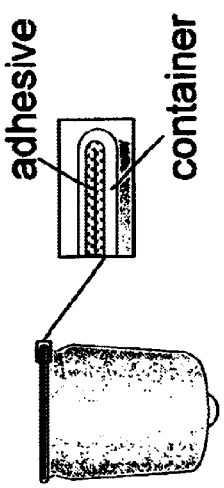
Figure 2C:
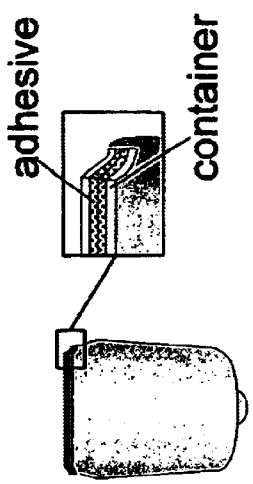
Figure 2D:
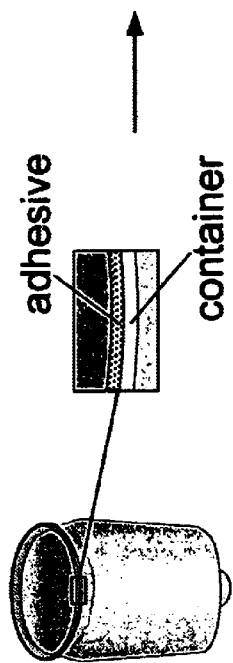
Figure 2E:
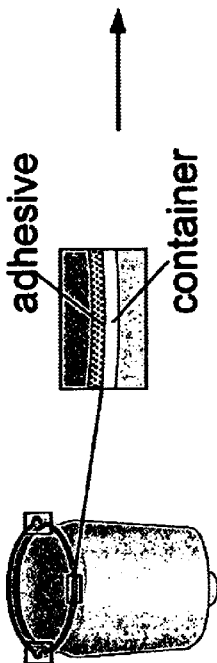
Figure 2F:
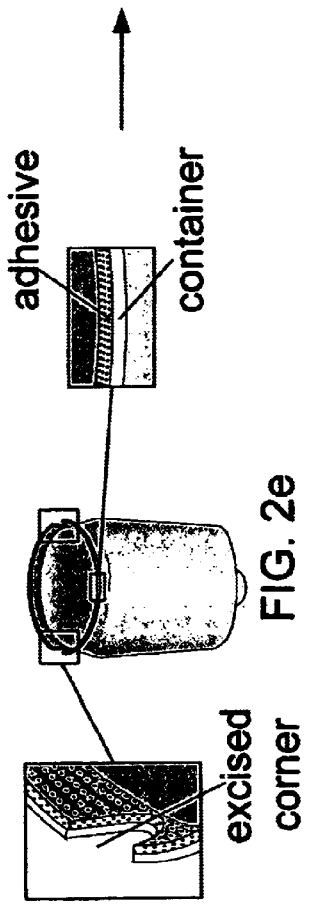

Opposite regions of an adhesive band may be brought into contact with each other to seal the collected semen inside the container (see, e.g., FIGS. 2b, 2d and 2f). To facilitate closure, the adhesive bands may contain recessed grooves on opposite sides of the open edge (see, e.g., FIGS. 2c and 2d) that provide the end user with a visual and/or tactile guide for sealing the device. These grooves may optionally containing thinner layers of container, cushion, or adhesive material that allow the open edge to bend and seal better.). Alternatively, to facilitate closure, the adhesive bands may contain excised corners on opposite sides of the open edge (see, e.g., FIGS. 2e and 2f) that also provide the end user with a visual and/or tactile guide for sealing the device.

The adhesive band is preferably covered with a removable protective strip that keeps the adhesive from adhering to any surface until the device is ready to be adhered (see, e.g., FIGS. 3a and 3b). The protective strip may contain a tab (see FIG. 3a) that may be pulled to remove the protective strip.

The device of the present invention may also further comprise a pressure "zipper" for sealing collected semen inside the container (see, e.g., the blue bands in FIGS. 1g–1i). The term "zipper" denotes any combination of elements present on two surfaces that, when the elements of one surface are pressed against the elements of the other surface, mechanically fixes one surface to another and does not allow passage of fluids between one side of the zipped region (e.g., the inside of the container) and the other side (e.g., the open edge of the container). A preferred example is a Zip-loc™ "zipper." The "zipper" thus may be zipped to seal the collected semen inside the container. The "zipper" permits medical personnel to obtain multiple semen samples at different times without tearing the container and without having to distribute the semen into multiple containers.

The device may further comprise a pre-cut discontinuous line located between different adhesive bands (see, e.g., FIG. 1f) or between an adhesive band and a "zipper" (see, e.g., FIG. 1i). The precise location of the pre-cut line is immaterial, so long as it does not interfere with the sealing function of the adhesive band or the "zipper." The pre-cut line may be torn or cut to separate the adhesive band away from remainder of the sealed container with the collected semen.

The device preferably further comprises a flexible protruding region (see, e.g., FIGS. 1c–1i and FIGS. 2–5) that may be retracted to allow the container to stably rest upon on a surface (see, e.g., FIG. 4). The shape of the protruding region is not critical; in FIGS. 1–5 the protruding region is shaped like a hollow nipple. The dimensions of the protruding region are generally not critical (the main requirement is that the device fits comfortably and snugly on the penis of the semen donor). The protruding region may have a diameter of about 0.2 to about 2 cm. and may protrude from about 0.2 to about 2 cm. in length at the tip of the container that is distal to the open edge. The protruding region may be cut to transfer collected semen to a second container such as a test tube (see, e.g., FIG. 5).

The device of the present invention may optionally be sterile. Sterility may be achieved by any method known in the art, including but not limited to:

heat treatment such as boiling;

heat treatment at high temperature and pressure as in an autoclave;

exposure to radiation, such as ultraviolet radiation or a radioactive source;

exposure to a sterilizing solution such as alcohol (e.g., 30% isopropanol).

Once sterilized, sterility may be maintained by sealing each device, or selected numbers of devices, inside individual sterile, airtight containers, such as sterile plastic or paper bags, which are opened only by when the device is to be used.

The device of the present invention may optionally be colored, either by mixing a pigment or combination of pigments with the material of the container, or by placing a layer of pigment or combination of pigments on the device. The color may be transparent or opaque, and it may, for example, match the color of the skin of the semen donor. Different pigments may be used to generate any desired pattern. The pigments should preferably be pharmaceutically acceptable. The pigments should preferably not contaminate the collected semen, for example because they are immovably bonded to or combined with the container material and/or because they are applied only to the outside surface of the container.

The device of the present invention may optionally be scented, either by mixing a scent or combination of scents with the material of the container, or by placing a layer of scent or combination of scents on the device. The scent should preferably be pharmaceutically acceptable. The scent should preferably not contaminate the collected semen, for example because it is combined with the container material and/or because it is applied only to the outside surface of the container.

The device of the present invention may further comprise a medicament, such as: a general antibiotic, an antiviral, an antifungal, an antibacterial, a compound that inhibits the growth of a specific target group of organisms (e.g., an inhibitor of gram negative bacteria), a hormone, a nucleic acid, an antibody, an immune system modulator such as a cytokine, a fertility enhancing composition such as Ham's F-10 tissue medium, and any combination thereof.

The device of the present invention may also comprise a reactive or indicator material that may be used to detect a property of the collected semen, such as pH or temperature or presence or concentration of a desired analyte such as sodium, ATP, sperm markers, prostate markers.

The device of the present invention may also further comprise a composition of matter that may be used to alter a property of the collected semen, such as a buffer for controlling the pH of the collected semen, or a salt composition, or a detergent, or any combination thereof.

The device of the present invention may further comprise a region for storing desired information. The desired information may include demographic data of the semen donor (e.g., species, name, age, sex, medical history, vital medical statistics such as past or present medical diseases or known medical susceptibility, genotypic information, family medical history, sperm count, sperm motility index), and/or the date the semen was collected, and/or frozen, and/or used; and/or what the semen was used for. The information may further include warnings or cautions, such as that the contents are biological materials, or biohazards. The information may also be calibrated lines that indicate the volume of collected semen inside the device (e.g., lines that measure between at least 0.1 and 20 ml, for example in 0.1 mL increments or in 0.5 mL increments). The region for storing desired information may simply be an area of the surface of the container that can be handwritten on, for example a printed colored square, or printed lines on a colored background. Alternatively, the region for storing desired information comprises a machine-readable element, such as for example a bar code or a micro-chip. This desired information may be pre-stored in machine-readable form, and it may be in a read-only format. In addition, the region for storing desired information may comprise a machine-writable element into which desired information may be encoded at will in a machine-readable format.

Another main embodiment of the present invention is a method for collecting semen, comprising the steps of
placing on a glans of a penis a device for collecting semen, wherein said device comprises a container having an opening that fits on a glans of a penis, wherein
said opening has an adhesive material that detachably adheres the device to the penis;
inducing the penis to ejaculate;
detaching the device from the penis together with the ejaculated semen; and
sealing the collected semen inside the detached device.

In one embodiment, the collected semen is sealed by adhering the adhesive band to itself. Alternatively, the device further comprises a zipper and the method further comprises sealing the collected semen in the device by zipping the zipper.

The method of the present invention may also comprise adding a medicament to the collected semen, and/or dialyzing the collected semen against a solution having a desired composition, and/or freezing the collected semen.

Another main embodiment of the present invention is a kit, comprising a device for collecting semen, and instructions for using the device to collect semen. The kit may further include a medicament that may be added to the collected semen, and/or a composition of matter that may be used to detect a property of the collected semen, and/or a composition of matter that may be used to alter a property of the collected semen, and instructions for their use. The kit may further include devices for reading machine-readable information, and devices for entering machine-writable information.

The features and advantages of the device of the present invention may perhaps be best illustrated by comparison with a condom. To collect semen with a condom, at first, the user places a rolled condom on the glans of the penis and then unfolds it completely over the shaft of the penis with care to prevent air from entering into the condom. The condom body fits the penis as snugly as possible to prevent the secreted semen from leaking.

There is a considerable difference in feeling between wearing and not wearing a condom. First, a conventional condom is inconvenient to put on and taken off. In putting on the condom, the wearer smears his fingers with a wax, lubricant or the like applied over the outer surface of the condom, which may contaminate the semen sample. The wax lubricant is smeared to the outer surface of the penis as well as the inner surface of the condom by the lubricant smeared fingers, therefore, the wearer feels uncomfortable because the lubricant blocks the pores in the skin of the glans. Furthermore, the snug fit of the condom often gives rise to a somewhat stuff and uncomfortable enclosed feeling. In addition, by covering the bulk of the penile skin surface, the typical condom reduces penile sensation (U.S. Pat. Nos. 6,250,303 and 6,145,507 both describe abbreviated condoms that fit on the glans of the penis. However, (1) those inventions are expressly intended to be used for intercourse; these patents do not teach or suggest semen collection and (2) the devices of the present invention are not intended nor will they be used for intercourse). Thus, the present invention provides comfortable and satisfaction while maximizing the skin contact area during semen collection.

C. Exemplary Uses of the Invention

1. Fertility studies

The semen collected with the devices and according to the methods of the present invention may be used to test the fertility of the collected sperm.

According to recent studies, male infertility (e.g. defective spermatogenesis or testicular obstruction) is responsible almost 40% of the time that a couple is unable to conceive a child. For a semen sample to be considered fertile according to standards set by the World Health Organization (WHO), at least two 1.5–5.0 milliliter ejaculate volumes obtained from a male should contain a sperm density of greater than 20 million spermatozoa/mL and/or a percent motility of 60% with a forward progression greater than 2 (on a 1–4 scale). In addition, the semen samples should show no evidence of sperm agglutination, leukocytospermia (pyospermia) or hyperviscosity (Sigman, M., et al., Evaluation of the non-fertile male. In: Lipschultz, L. I. and S. S. Howards, eds. Infertility in the Male, 2nd ed. Chicago: Mosby-Year Book, 1991; p.184). A leukocyte count in semen that is greater than 1 million/ml is diagnostic by WHO criteria of leukocytospermia, a condition that is frequently associated with genitourinary infection, antisperm antibodies and male infertility.

By convention, male infertility is diagnosed based on low sperm motility and/or count. However, motility analyses can produce false negatives, since fertile sperm may appear non-motile due to damage sustained during processing. With regard to sperm count, 20 million spermatozoa/mL or greater is generally considered to be in the fertile range. However, non-motile, non-fertile sperm can be included in the count. Sperm count and motility are typically assessed using commercially available instruments, such as light microscopes and computerized videoanalysis systems.

2. Breeding and artificial insemination

The semen collected with the devices and according to the methods of the present invention may be used for breeding and artificial insemination.

The device of the present invention is particularly useful to collect semen for breeding operations in selected animals, notably humans and domestic animals such as cattle, horses, sheep, goats, pigs, etc., or endangered animal species. It enables many more females to become impregnated by a male of having desirable genetic traits, for example a bull that has already bred offspring producing high milk or meat yields. Artificial insemination has also proved useful in preventing the spread of certain venereal diseases such as dourine in horses and trichomonas infection in cattle. Another use is for making crosses between animals belonging to varieties in which the disparity in size is so great that coitus between them is difficult or impossible. Crosses can also be made between different species where there is difficulty in getting normal mating to take place. In addition, artificial insemination can be used to prevent the extinction of endangered species.

The collected semen is optionally diluted for purposes of preservation and to avoid any depletion of sperm survival. This is normally accomplished by mixing the collected semen with a "dilutor", the function of which is to increase the volume of the sperm-containing liquid in order to multiply the number of doses which can be made available from a given semen sample, to prevent temperature shock, to preserve the spermatozoa for long periods with a minimum fall in fertility, and to have a buffering effect. Typical of such dilutors are for example, egg yolk, mixtures of egg yolk with glycine or various citrates and phosphates, and milk including skimmed milk, homogenized whole milk, milk containing egg yolk, glycine and glycerol, powdered milk, and even cream. Antibiotics such as sulfanilamide, penicillin, and streptomycin may also be added. After the collected semen has been diluted, with whatever dilutor is chosen, it is then cooled and frozen in order to maintain fertility for as long a period as is possible. Thus, the diluted and cooled semen may be stored frozen in solid carbon dioxide at about $-79°$ C., or in liquid nitrogen at about $-193°$ C.

The device of the present invention may also comprise a reactive or indicator material that may be used to detect a property of the collected semen, such as pH or presence or concentration of a desired analyte such as sodium, ATP, sperm markers, prostate markers. The reactive or indicator material may include, for example, a pH sensitive dye, a ligand for a particular molecule, an enzyme, an antibody, and/or colored reagents.

The device of the present invention may also further comprise a composition of matter that may be used to alter a property of the collected semen, such as a buffer for controlling the pH of the collected semen, or an antibody, or a hormone, or a salt composition, or a detergent, or any combination thereof 3. Collection of biological fluids other than semen Although the preceding text has focused on the collection of semen, the devices and methods of the present invention are also useful for collecting other biological fluids such as blood, saliva, wound exudates, or urine. The container is adhered over a source of a given bodily fluid, so that the source or body opening faces the interior of the container, and the container is allowed to remain adhered until a desired amount of fluid is collected. The device is then detached, sealed and processed as desired.

It will be apparent from the foregoing that many other variations and modifications may be made in the structures and methods described herein without departing substantially from the essential concepts of the present invention. Accordingly, it should be clearly understood that the particular and specific forms of the invention described herein and depicted in the accompanying drawings are exemplary only and are not intended as limitations of the scope of the present invention. All publications and patents referenced herein are hereby incorporated by reference.

What is claimed is:

1. A device for collecting fertile semen suitable for use in fertilization protocols, comprising a sealable container having at least one sealing region for sealing collected semen inside the container, wherein said container comprises:
   a.) an opening that contains a band of an adhesive material that detachably adheres the opening of said device to a glans of a penis; and
   b.) a medicament selected from the group that includes medicaments that preserve the fertility of collected semen and medicaments that enhance the fertility of collected semen.

2. A device according to claim 1, wherein said container further comprises a protruding region that may be cut to transfer collected semen to a second container.

3. A device according to claim 1, wherein said container is made of a material that is impermeable to semen.

4. A device according to claim 1, wherein said container is made of a selectively permeable material.

5. A device according to claim 1, wherein said device comprises a zipper for sealing collected semen inside the container.

6. A device according to claim 5, wherein said device further comprises a precut line between the adhesive region and the zipper.

7. A device according to claim 1, wherein said device is sterile.

8. A device according to claim 1, wherein said device is colored.

9. A device according to claim 1, wherein said device is scented.

10. A device according to claim 1, wherein said device contains a medicament selected from the following list: a general antibiotic, an antiviral, an antifungal, an antibacterial, a compound that inhibits the growth of a specific target group of organisms, (an inhibitor of gram negative bacteria), a hormone, a nucleic acid, an antibody, an immune system modulator; a cytokine, a salt composition, a buffer, a composition of matter that detects a property of semen, a composition of matter that alters a property of semen, a ligand for a molecule that may be present in semen sample, and any combination thereof.

11. A device according to claim 1, wherein said device contains a region for storing desired information.

12. A device according to claim 11, wherein said region for storing desired information comprises a region that can be handwritten on.

13. A device according to claim 11, wherein said region for storing desired information comprises a machine-readable element.

14. A device according to claim 13, wherein desired information is pre-stored in machine-readable form.

15. A device according to claim 14, wherein desired information is entered at will in machine-readable form.

16. A device according to claim 13, wherein said information is information concerning the semen donor.

17. A device according to claim 16, wherein said information is selected from the following list: demographic data, species, name, age, sex, medical history, vital medical statistics, past medical diseases, present medical diseases, medical susceptibility, genotypic information, family medical history, and any combination thereof.

18. A device according to claim 13, wherein said information is information concerning the semen sample.

19. A device according to claim 18, wherein said information is selected from the following list: sperm count, sperm motility index, volume of collected semen, the date a semen sample was collected, identity of a composition of matter that was added to a sample, the date a composition of matter that was added to a sample, the date that a semen sample was frozen, each date a semen sample was used; what the semen was used for, and any combination thereof.

20. A device according to claim 1, wherein said device is made of a temperature resistant material.

21. A method for collecting fertile semen suitable for use in fertilization protocols, comprising:
 a.) placing on a glans of a penis a device for collecting semen, comprising a sealable container having at least one sealing region for sealing collected semen inside the container, wherein said device comprises a container having
  an opening that fits on a glans of a penis, wherein said opening has a band of an adhesive material that detachably adheres the device to a glans of a penis, and
  a medicament selected from the group that includes medicaments that preserve the fertility of collected semen and medicaments that enhance the fertility of collected semen;
 b.) inducing the penis to ejaculate;
 c.) detaching the device from the penis together with the ejaculated semen; and
 d.) sealing the collected semen inside the detached device.

22. A method according to claim 21, wherein the collected semen is sealed by adhering the adhesive band to itself.

23. A method according to claim 21, wherein said device further comprises a zipper and the method further comprises sealing the collected semen in the device by zipping the zipper.

24. A method according to claim 21, wherein said container further comprises a protruding region for collecting semen.

25. A method according to claim 21, wherein said medicament is selected from the following list: a general antibiotic, an antiviral, an antifungal, an antibacterial, a compound that inhibits the growth of a specific target group of organisms, an inhibitor of gram negative bacteria, a hormone, a nucleic acid, an antibody, an immune system modulator, a cytokine, a salt composition, a buffer, a composition of matter that is used to detect a property of semen, a composition of matter that alters a property of semen, a ligand for a molecule that may be present in semen sample, and any combination thereof.

26. A method according to claim 21, further comprising dialyzing the device with the collected semen.

27. A method according to claim 21, wherein the device comprises a cup and a flexible material and the method further comprises discarding the flexible material and sealing the semen by capping the cup.

28. A kit for collecting fertile semen, comprising:
 a.) a device for collecting fertile semen, wherein said device comprises a sealable container having at least one sealing region for sealing collected semen inside the container wherein said container comprises:
  an opening that fits on a glans of a penis, wherein said opening has a band of an adhesive material that detachably adheres the device to a glans of a penis, and
  a medicament selected from the group that includes medicaments that preserve the fertility of collected semen and medicaments that enhance the fertility of collected semen; and
 b.) instructions for using the device to collect semen.

29. A kit according to claim 28, further comprising a device for storing machine-readable information.

30. A kit according to claim 28, further comprising a machine for reading machine-readable information.

31. A kit according to claim 28, further comprising a machine for writing machine-readable information.

32. A device for collecting fertile semen suitable for use in fertilization protocols, comprising a sealable container having at least one sealing region for sealing collected semen inside the container, wherein said container comprises:
 a.) an opening that contains a band of an adhesive material that detachably adheres the opening of said device to a glans of a penis; and
 b.) a region for storing desired information that comprises a machine-readable element.

33. A device according to claim 32, wherein said container further comprises a protruding region that may be cut to transfer collected semen to a second container.

34. A device according to claim 32, wherein said container is made of a material that is impermeable to semen.

35. A device according to claim 32, wherein said container is made of a selectively permeable material.

36. A device according to claim 32, wherein said device comprises a zipper for sealing collected semen inside the container.

37. A device according to claim 36, wherein said device further comprises a precut line between the adhesive region and the zipper.

38. A device according to claim 32, wherein said device is sterile.

39. A device according to claim 32, wherein said device is colored.

40. A device according to claim 32, wherein said device is scented.

41. A device according to claim 32, wherein said device contains a medicament that preserves the fertility of semen, selected from the following list: a general antibiotic, an antiviral, an antifungal, an antibacterial, a compound that inhibits the growth of a specific target group of organisms, an inhibitor of gram negative bacteria, a hormone, a nucleic acid, an antibody, an immune system modulator, a cytokine, a buffer, a salt composition, a buffer, a composition of matter that is used to detect a property of semen, a composition of matter that alters a property of semen, a ligand for a molecule that may be present in semen sample and any combination thereof.

42. A device according to claim 32, wherein desired information is pre-stored in machine-readable form.

43. A device according to claim 42, wherein desired information is entered at will in machine-readable form.

44. A device according to claim 32, wherein said device is made of a temperature resistant material.

45. A device according to claim 32, wherein said information is information concerning the semen donor.

46. A device according to claim 45, wherein said information is selected from the following list: demographic data donor, species, name, age, sex, medical history, vital medical statistics, past medical diseases, present medical diseases, medical susceptibility, genotypic information, family medical history, and any combination thereof.

47. A device according to claim 32, wherein said information is information concerning the semen sample.

48. A device according to claim 47, wherein said information is selected from the following list: sperm count, sperm motility index, volume of collected semen, the date a semen sample was collected, identity of a composition of matter that was added to a sample, the date a composition of matter that was added to a sample, the date that a semen sample was frozen, each date a semen sample was used; what the semen was used for, and any combination thereof.

* * * * *